United States Patent [19]

Sela et al.

[11] 4,075,194

[45] Feb. 21, 1978
:::

[54] NOVEL SYNTHETIC UNDECAPEPTIDE AND CLINICAL ASSAY

[75] Inventors: Michael Sela; Ruth Arnon, both of Rehovot; Samario Chaitchik, Tel-Aviv, all of Israel

[73] Assignee: Yeda Research and Development Co., Ltd., Rehovot, Israel

[21] Appl. No.: 749,093

[22] Filed: Dec. 9, 1976

[51] Int. Cl.$^2$ .................... C07C 103/52; A61K 39/00
[52] U.S. Cl. .............................. 260/112.5 R; 424/12; 424/88
[58] Field of Search .................. 260/112.5 R; 424/172

[56] References Cited

PUBLICATIONS

R. Aron, et al., Chem. Abst. 85, 1976, p. 121543t.
A. M. Reuter, et al., Chem. Abst. 86, 1977, p. 153709p.
T. S. Edgington, et al., Chem. Abst. 86, 1977, p. 153710g.

*Primary Examiner*—Delbert R. Phillips
*Attorney, Agent, or Firm*—Browdy and Neimark

[57] ABSTRACT

A novel synthetic peptide corresponding to the eleven amino acid residues of the NH$_2$-terminal portion in the sequence of carcinoembrionic antigen (CEA) has been synthesized and this was attached by means of a water-soluble carbodiimide reagent to multichain poly(DL)-alanine as well as to bovine serum albumin. The resulting macromolecular conjugates provoked rabbit anti-CEA(1-11) peptide antibodies and a novel assay was developed for ascertaining the presence of adenocarcinomas of the digestive tract, pancreas and breast, based on said novel compositions of matter.

3 Claims, No Drawings

NOVEL SYNTHETIC UNDECAPEPTIDE AND CLINICAL ASSAY

SUMMARY OF THE INVENTION

The present invention relates to a novel composition of matter, namely to a novel undecapeptide corresponding to the 11 amino acid residues of the $NH_2$-terminal portion in the sequence of carcinoembrionic antigen (CEA) has been synthesized by the solid phase technique. The synthetic CEA(1-11) peptide was attached by means of a water-soluble carbodiimide reagent to multichain poly (DL-alanine) as well as to bovine serum albumin, resulting in two further novel compounds. Both the novel macrmolecular conjugates provoked in rabbit anti-CEA(1-11) peptide antibodies. The specifity of this immunological system and the crossreactivity between the peptide and intact CEA were investigated both by the passive hemagglutination technique and by modified bacteriophage inactivation. Hemagglutination experiments showed that not only anti-CEA(1-11) sera but also anti-CEA sera, agglutinated CEA(1-11)-coated sheep erythrocytes and both these reactions were inhibited with CEA(1-11) peptide. In experiments with the chemically modified bacteriophage technique CEA(1-11)-coated phage was efficiently inactivated with antisera against the CEA(1-11) conjugates, and the inactivation reactior could be totally inhibited with the free peptide. The semipure CEA, but not the pure protein, was able to inhibit the phage inactivation, but less efficiently. The above results were basis for a novel test and assay method according to the invention. Sera of a number of cancer patients were tested for their capacity to inhibit the inactivation of CEA(1-11)-coated phage by means of anti-CEA(1-11) antiserum. The results indicate that sera from a large proportion of patients with adenocarcinomas of the digestive tract, pancreas and breast are capable of inhibiting the above inactivation, whereas most normal sera do not result in such inactivation.

BACKGROUND OF THE INVENTION

The carcinoembryonic antigen (CEA) of the colon is a glycoprotein isolated and identified by Gold and his colleagues in 1965, J. Exp. Med. 122, (1965) 467-481. This protein, characteristic of many kinds of cancer tissues, has a molecular weight of about 200,000, Krupey et al. J. Exp. Med. 128 (1968) 387 and Coligan et al. Immunochemistry, 9 (1972) 377. It is rather heterogeneous and 50-75% of its content is of a polysaccharide nature. Great interest in CEA arose as a result of the possibility that its detection or quantitation may serve as an efficient method of cancer diagnosis, Thomson, et al., Proc. Natl. Acad. Sci. USA 64 (1969) 161. Several Radioimmunoassays were developed for the detection of CEA and have been used on tens of thousands of serum samples of cancer patients and normal individuals, Egan et al. Immunochemistry 9 (1972) 289. Many limitations were observed concerning successful use of such radioimmunoassays. These include large numbers of false negative results, as well as cross-reactions with nondigestive-tract cancerous and normal tissues. It has also been reported that in some cases there is an immunological cross-reaction between CEA and blood group substances, Turner et al. J. Immunol. 108 (1972) 1328.

CEA being a glycoprotein, it is reasonable to assume that some of its antigenic determinants may be of polysaccharide nature, whereas others may be of protein nature. Among the protein determinants one might distinguish between sequential ones, namely those that lead to antibodies capable of reacting with a short peptide segment derived from that region of the molecule, and conformation-dependent determinants that lead to the production of antibodies capable of reacting with a certain region of the native protein but that may not react with the protein after its denaturation. In view of the interest in CEA it was thought to be advisable to try to synthesize a portion of the molecule and enquire whether antibodies against such a synthetic material are able to react with either native CEA or its partial degradation products. Terry et al. J. Exp. Med. 136 (1972) 200, reported recently the amino terminal sequence derived from CEA. The sequence found is: Lys-Leu-Thr-Ile-Glu-Ser-Thr-Pro-Phe-Asn-Val-Ala-Glu-Gly-Lys-Glu-VaL-Leu-Leu-Leu-Val-His-Asn-Leu. The same sequence has been found in five other preparations of CEA isolated from tumor tissue.

We have shown previously that it is possible to prepare by stepwise synthesis, a peptide of 19 amino acids corresponding to a portion of the hen egg-white lysozyme moleculre, Arnon et al. Pro.Nat.Acad. Sci. USA 62 (1969) 163. This peptide was attached covalently to a synthetic polymer and the resulting conjugate was shown to provoke antibodies capable of reacting with native lysozyme, Maron et al. Biochem. 10 (1971) 763. In the case of CEA our desire was to prepare a synthetic peptide, convert it into an immunogenic macromolecule and see: (a) whether antibodies to the peptide are capable of recognizing the peptide in intact CEA; (b) whether at least some of the antiboeies made against CEA may recognize the peptide. Should the answer to these two questions be negative, the possibility still remains that whilethe peptide in intact CEA cannot be recognized by antibodies specific to this peptide, nevertheless, the antibodies might recognize the peptide in partial degration products of CEA. It was considered of interest to find out whether antibodies of the peptide could detect some crossreactive material in sera of patients with colonic cancer but not in normal individuals.

DESCRIPTION OF THE PREFERRED EMBODIMENTS

The invention is illustrated with reference to the following preferred embodiments, which are to be understood in an illustrative and not in a limitative manner.

a. Materials

Reagents. $N^\alpha$-t-Butyloxycarbony (Boc)-L-amino acid derivatives were either purchased from Miles-Yeda Ltd., or were prepared in our Institute. The blocked groups of the amino acid side chains included the benzyl ethers of tyrosine, serine, and threonin, the $\gamma$-benzyl ester of glutamic acid, and carbobenzoxy derivatives of the $\epsilon$-amino function of lysine. Chloromethylated resin was purchased from Schwarz/Mann. Dicyclohexyl carbodiimide was purchased from Fluka (Switzerland) and 1-ethyl-3-(3-dimethylaminopropyl) carbodiimide (ECDI), from Ott Chemicals. Sephadex G-10 was obtained from Pharmacia (Sweden) and complete Freund's adjuvant from Difco (Detroit, Mich.). All solvents were analytical grade or the best grade available.

CEA. Purified CEA, prepared from colonic tumor tissue by a sequence of procedures including perchloric acid extraction, column chromatography on Sephadex G-200, and preparative block electrophoresis on Sephadex G-25. Crude CEA was the dialyzed and lyophilized ammonium sulfate fraction precipitated from perchloric acid extract of the tumor tissue.

Human Serum Samples. Serum samples were taken from patients with cancer of various systems as well as from patients suffering from other nonmalignant diseases and normal individuals at different ages. The cancer patients included those suffering from cancer of the digestive tract (colon, stomach, pancreas, esophagus, and rectum), tumors of the urinary tract, ovarian tumors of different histological types, breast tumors of various histological types, melanoma, lymphoma (non-hodgkin's), soft tissue sarcoma, and tumors of the central nervous system. All cancers were characterized by cytological and histological examination. Normal individuals were either young people without any known disease, or elderly people (over 65 years old) with cardiovascular diseases and Parkinson syndrome.

b. Methods:

Synthesis of the Peptide. The CEA(1-11) peptide was synthesized by the solid phase technique, Merrifield, Biochem. 3 (1964) 1385. The Boc derivative of valine (or leucine) was esterified to 5 g of chloromethylated resin (1.2 meq of Cl/g). The resulting resin contained 0.36 mmol of valine per g.

The progress of synthesis was monitored by removal of samples after coupling three or four amino acid residues, and amino acid analysis (Beckmann model 120 B analyzer) following hydrolosis under reduced pressure in 6 M HCl in dioxane for 22 hr at 110°.

After cleavage from the resin 650 mg of crude peptide were obtained (a yield of 35%).

Purification of the Peptide. The peptide cleaved from the resin was purified by gel filtration on a Sephadex G-10 column (2.5 × 110 cm) in 0.1 M acetic acid. The absorbance at 230 nm was monitored in a Zeiss Model PMQII spectrophotometer, and fractions under the main peak were pooled and lyophilized. The purity of the peptide was assessed by amino acid analysis. The peptide was further purified by high voltage paper electrophoresis at pH 1.9 and 2000 V, for 1 hr. The electrophoretic pattern showed one main spot which gave amino acid analysis in agreement with the expected values of the various amino acids, and two other weaker spots, which showed smearing. The main spot was eluted from the paper with 0.2 M acetic acid and lyophilized. The yield of this peptide out of the total material cleaved from the resin was 30%.

Preparation of the Conjugates. CEA(1-11) was attached to multipoly (DL-alanyl)--poly(L-lysine) ( a graft polymer of DL-alanine polymers on a polylysine backbone, designated A--L, Sela et al. J. Am. Chem. Soc. (1956) 78, 746), as well as to bovine serum albumin (BSA) and ribonuclease (RNase), using ECDI as a coupling reagent. ECDI and the peptide were dissolved in 0.05 M sodium phosphate buffer, pH 7.5, and any indissolved material was removed by centrifugation. A solution of A--L was then added to a mixture of these two solutions. The reaction was allowed to proceed overnight with stirring at room temperature. The unreacted peptide and coupling agent were removed by dialysis and the conjugate was lyophilized.

A similar procedure was employed for the coupling of the peptide to BSA and to RNase. High voltage paper electrophoresis showed that the resulting conjugates did not contain any free peptide.

Immunization Procedure. Antisera against the CEA(1-11) peptide were obtained by immunizing rabbits with CEA(1-11) as the free peptide and with the two conjugates CEA(1-11)-A--L and CEA(1-11)-BSA. The rabbits were immunized by multisite intradermal injections in complete Freund's adjuvant. Each rabbit received two injections of 4 mg at 2-week intervals and was subsequently bled weekly from the marginal vein, starting 1 week after the last injection.

Hemagglutination and Inhibition of Hemagglutination. Sheep erythrocytes were treated with formalin, tanned, and coated with the CEA(1-11) peptide or with the conjugates (CEA(1-11)-A--L or CEA(1-11)-BSA, Herbert: Handbook Exp. Immun., Oxford (1964), 720, Blackwell, Sci. Pub.

Passive microhemagglutination tests, Kabat: Structural Concepts in Immun. and Immunochem. (1968), Holt, Reinhart and Winston, Inc., N.Y., were performed on disposable microtiter plates (Cooke Engineering Co., Alexandira, Va.) by 2-fold serial dilutions of antisera in phosphate-buffered saline (0.15 M NaCl-0.01 M sodium phosphate buffer, pH 7.0), containing 0.1% ovalbumin (twice crystallized, Schwarz/Mann). The plates were incubated at room temperature and read after 2 and 4 hr.

In inhibition experiments serial dilutions of the respective inhibitor were allowed to react for 30 min with the antisera (at the last dilution that had given positive agglutination) prior to the addition of the coated erythrocytes. Inhibition results were also read after 2 and 4 hr.

Inactivation and Inhibition of Inactivation of CEA(1-11)-coated T4 Bacteriophage. The preparation of CEA(1-11)-coated T4 bacteriophage was carried out according to the procedure described by Haimovich et al., Biochim. Biophys. Acta 207 (1970) 115, making use of glutaraldehyde as crosslinking agent. The resulting modified bacteriophage preparation was tested for inactivation with anti-CEA(1-11)-BSA serum, by incubation for 2½ hr at 37° in the presence of different dilutions of the antiserum, and monitoring the surviving phage by subsequent plating with bacteria.

In inhibition experiments the inhibitors were allowed to react at room temperature, overnight, with the amount of antiserum that would have caused approximately 90% inactivation of the bacteriophage conjugate, Haimovich et al. Biochim. Biophys. Acta 207 (1970) 125. The modified bacteriophage was then added to the mixture and the number of surviving phage was determined as described above. The percentage of inhibition was calculated from the extent of inactivation in the presence and in the absence of the inhibitor.

Synthesis and Characterization of CEA(1-11)

A novel synthetic undecapeptide corresponding to the first eleven amino acid residues from the amino-terminus of the CEA-sequence, with leucine replacing valine in the 11-position was synthesized. The synthesis was performed by the solid phase method, the attachment being: Resin-Leu-Asn(OPN)-Phe-Pro-Thr-(OBz)-Ser(Obz)-Glu(γ-Bz)-Ile-Thr-Leu-Lys(Z)-t-Boc, which was subsequently deblocked and removed from the resin by treatment with hydrofluoric acid to give the desired undercapeptide having the sequence Leu-Asn-Phe-Pro-Thr-Ser-Glu-Ile-Thr-Leu-Lys, wjerein Bz designates benzyl and NP designates nitrophenyl. The appropriately blocked t-butyloxycarbonyl derivatives of the required amino acids were used and the aminoacid composition of the resultant CEA(1-11) peptide, obtained after purification by gel filtration and high voltage paper electrophoresis is shown in Table 1.

Table 1.

| Amino acid composition of the synthetic CEA(1-11) peptide | | |
|---|---|---|
| Amino acid residue | Observed | Expected |
| Lys | 0.90 | 1 |
| Asp | 1.00* | 1 |
| Thr | 1.89 | 2 |
| Ser | 0.97 | 1 |
| Glu | 1.05 | 1 |
| Pro | 0.90 | 1 |
| Ile | 0.91 | 1 |
| Leu | 1.91 | 2 |
| Phe | 1.00 | 1 |

*The calculations were based on the assumption that the value for aspartic acid is 1.00.

Preparation of Antibodies with CEA(1-11) Conjugates of a Synthetic Antigen and a Protein.

The synthetic CEA(1-11) peptide was attached by means of a water-soluble carbodiimide reagent to a multichain polymer, the multi-poly (DL-alanyl)-poly(L-lysine), denoted A—L, as well as to bovine serum albumin (Table 2). The amount of CEA(1-11) peptide bound to the A—L carrier, as determined by amino acid analysis of the conjugate, was on the average 9.5 moles of peptide per 1 mole of A—L (molecular weight 100,000). It is assumed that the peptide was similarly attached to BSA. Whereas immunization with the free peptide CEA(1-11) led to antisera of low titer, both macromolecular conjugates produced anti-CEA(1-11) antibodies in rabbits (Table 3).

Table 2.

| Preparation of CEA(1-11) conjugates | | | | |
|---|---|---|---|---|
| | Amounts used for the coupling reaction (mg) | | | Amount CEA(1-11) bound (moles) per mole carrier |
| Conjugate | Carrier | CEA(1-11) | EDCI | |
| CEA(1-11)-BSA | 109 | 15 | 15 | n.d. |
| CEA(1-11)-A—L | 60 | 15 | 15 | 9.5 | n.d., not determined

Table 3.

| Passive hemagglutination with CEA(1-11)-A—L-coated sheep erythrocytes | | |
|---|---|---|
| Antiserum against | Hemagglutination titer | Inhibitor* |
| CEA(1-11) | 1:4 | n.d. |
| CEA(1-11)-A—L | 1:128 | CEA(1-11) (1μg/ml) Crude CEA (200 μg/ml) |
| CEA(1-11)-BSA | 1:32 | CEA(1-11) (10 μg/ml) Crude CEA (500 μg/ml) |
| Pure CEA | 1:64 | CEA(1-11) (1 μg/ml) |
| Crude CEA | 1:16 | CEA(1-11) (100 μg/ml) Crude CEA (30 μg/ml) |
| BSA | 1:4 | n.d. |
| T4-Bacteriophage | < 1:4 | n.d. |
| Hexosaminidase | < 1:4 | n.d. | n.d., not determined.
*The inhibition experiments were done with serum concentration twice that of the hemagglutination titer; the numbers in parentheses indicate the lowest concentration of inhibitor that still prevents agglutination.

Specificity of Anti-CEA(1-11) Antibodies.

The specificity of the antibodies elicited by the CEA(1-11) conjugates was investigated by using two techniques - passive hemagglutination and modified bacteriophage inactivation. From passive hemagglutination experiments (Table 3) it emerges that some cross-reactivity exists between CEA(1-11) peptide and native CEA. This was demonstrated on the one hand by the capacity of anti-CEA sera, prepared both against pure and crude protein preparations, to agglutinate sheep erythrocytes coated with CEA(1-11)-A—L, and on the other hand, by the capacity of intact CEA in the crude CEA preparation to inhibit the specific hemagglutination of the coated erythrocytes with anti-CEA(1-11) antibodies. The carrier A—L had no inhibitory effect. Nonrelated antisera did not cause any agglutination of the coated erythrocytes.

For experiments with the modified bacteriophage technique, we used a T4 bacteriophage preparation to which the free CEA(1-11) peptide was attached. This modified phage preparation was efficiently inactivated by the anti-CEA(1-11)-BSA serum (Table 4). The inactivation followed firstorder kinetics, reaching 95% inactivation after a 2 hr reaction at a final dilution of 1:67,000. This inactivation could be inhibited either by the free CEA(1-11) peptide or, to a lesser extent, by the crude preparation of intact CEA (Table 5). No inhibition was observed with a pure preparation of CEA.

Table 4.

| Inactivation of CEA(1-11)-T4 by anti-CEA(1-11)-BSA serum. Reaction was for 2 hours at 37°. | | |
|---|---|---|
| Serum concentration | Surviving Phage (PFU) | Inactivation (5) |
| 0 | 450 | |
| $0.37 \times 10^{-5}$ | 230 | 49 |
| $0.75 \times 10^{-5}$ | 86 | 81 |
| $1.12 \times 10^{-5}$ | 50 | 89 |
| 1.50 | 30 | 93 |

In a semilogarithmic plot the data of the surviving phage give a linear relationship with the serum concentration.

Table 5.

| Inhibition of inactivation of CEA(1-11)-T4 by anti-CEA(1-11)-BSA serum with CEA(1-11) pepside and crude CEA preparation | | |
|---|---|---|
| Inhibitor concentration (μg/ml) | Inhibition (%) | |
| | CEA(1-11) | Crude CEA |
| 0.001 | 0 | — |
| 0.0033 | 38 | 24 |
| 0.01 | 64 | 30 |
| 0.033 | 82 | 42 |
| 0.1 | 92 | 48 |
| 0.33 | 100 | 76 |
| 1 | 98 | 89 |
| 3 | 100 | 90 |

Cross-Reactivity of Human Sera with CEA(1-11)

In view of the fact that some cross-reactivity exists between CEA(1-11) and intact CEA, we have screened sera of cancer patients as well as normal individuals for their capacity to inhibit the inactivation of CEA(1-11)-T4 by anti-CEA(1-11) antiserum. The results are presented in Table 6.

As seen from the table, a high percentage of the patients with colonic, rectal, stomach, and pancreatic adenocarcinoma had effective inhibitory capacity in the CEA(1-11)-anti-CEA(1-11) system exerting between 50 and 88% inhibition. A small portion of patients with breast adenocarcinoma also effected inhibition, whereas sera of patients with nonrelevant cancers and nonrelevant diseases were negative, i.e., caused less than 40% inhibition. Normal young individuals were mostly negative but, among individuals older than 65 years, a higher percentage (5 out of 13) caused inhibition of 40% and above. An important observation was the lack of inhibition by sera from post-operation cases of colonic adenocarcinoma, whereas sera of the same patients before operation were highly inhibitory (70-82% inhibition).

Table 6.

Inhibition by human sera of inactivation of CEA(1-11)-T4 by anti-CEA(1-11)-BSA

| Clinical diagnosis | Positives (>40% inhibition) | Total | % positives |
|---|---|---|---|
| Adenocarcinoma of colon, rectum, and stomach | 30 | 34 | 88 |
| Adenocarcinoma of colon, rectum, and stomach, post operaational without matastases | 0 | 5 | 0 |
| Pancreatic adenocarcinoma | 3 | 3 | 100 |
| Breast adenocarcinoma | 9 | 14 | 64 |
| Lung tumors | 0 | 6 | 0 |
| Other neoplasias | 2 | 14 | 14 |
| Nonmalignant diseases | 0 | 2 | 0 |
| Normals (25–40 years old) | 2 | 26 | 8 |
| Normal (over 65 years old) | 5 | 13 | 38 |

The above results compare favorably with other assays known in the art and thus the novel assay method is of considerable value in clinical studies, and especially of patients after surgery of colonic adenocarcinoma.

It is to be stressed that it was not possible to predict in advance whether antibodies prepared against the NH$_2$-terminal region of CEA would react with the intact protein. In spite of the incapacity of the anti-CEA (1-11) antibodies to react with pure CEA, they are able to recognize something in most sera of patients with adenocarcinoma of the digestive tract which is not present in patients with other neoplasias or in normal individuals. It is apparent from the above that a synthetic fragment of CEA may be used in a sensitive immunoassay relevant to CEA. A similar fragment with an appropriate radioactive label may be utilized in an equivalent radioimmunoassay, based on the same immunological specifity.

We claim:

1. The synthetic undecapeptide corresponding to the terminal amino acid residues of the amino-terminal portion of carcinoembrionic antigen (CEA) of the sequence Leu-Asn-Phe-Pro-Thr-Ser-Glu-Ile-Thr-Leu-Lys.

2. A synthetic undecapeptide according to claim 1, bonded via a water-soluble diimide to a macromolecular carrier selected from the group consisting of multichain poly-DL-alanine, bovine serum albumin or ribonulcease.

3. A conjugate according to claim 2, wherein the coupling agent is ECDI (1-ethyl-3-(3-dimethylaminopropyl) carbodiimide.

* * * * *